(12) United States Patent
Manetta et al.

(10) Patent No.: US 10,387,613 B2
(45) Date of Patent: Aug. 20, 2019

(54) DISPLAYING STATUS OF MEDICAL LINES

(71) Applicant: Draeger Medical Systems, Inc., Andover, MA (US)

(72) Inventors: Amy M. Manetta, North Billerica, MA (US); Jacqueline Marie Mulcahy, Natick, MA (US); Thomas F. Meinert, Boxford, MA (US)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 953 days.

(21) Appl. No.: 14/816,991

(22) Filed: Aug. 3, 2015

(65) Prior Publication Data

US 2017/0039319 A1  Feb. 9, 2017

(51) Int. Cl.
*G06F 3/0484* (2013.01)
*G06F 19/00* (2018.01)

(52) U.S. Cl.
CPC .................... *G06F 19/321* (2013.01)

(58) Field of Classification Search
CPC .................... G06F 19/00; G06F 19/3481
See application file for complete search history.

(56) References Cited

U.S. PATENT DOCUMENTS

| | | | |
|---|---|---|---|
| 5,522,798 A | 6/1996 | Johnson et al. | |
| 5,527,289 A | 6/1996 | Foster et al. | |
| 5,573,502 A | 11/1996 | LeCocq et al. | |
| 5,782,805 A | 7/1998 | Meinzer et al. | |
| 5,830,150 A | 11/1998 | Palmer et al. | |
| 7,300,418 B2 | 11/2007 | Zaleski | |
| 7,693,697 B2 | 4/2010 | Westenskow et al. | |
| 7,945,452 B2 | 5/2011 | Fathallah et al. | |
| 7,970,624 B2 | 6/2011 | Anderson et al. | |
| 8,038,593 B2 | 10/2011 | Friedman et al. | |
| 8,038,642 B2 | 10/2011 | Tolvanen-Laakso et al. | |
| 8,250,483 B2 | 8/2012 | Blomquist | |
| 8,291,337 B2 | 10/2012 | Gannin et al. | |
| 8,317,752 B2 | 11/2012 | Cozmi et al. | |
| 8,398,592 B2 | 3/2013 | Leibner-Druska | |
| 8,437,835 B2 | 5/2013 | Nemoto | |
| 8,494,879 B2 | 7/2013 | Davis et al. | |
| 8,612,257 B2 | 12/2013 | Zaitsu et al. | |
| 2003/0065537 A1* | 4/2003 | Evans | G06F 19/326 705/2 |
| 2004/0168988 A1* | 9/2004 | Ikeda | A61M 1/16 210/744 |

(Continued)

*Primary Examiner* — Rayeez R Chowdhury
(74) *Attorney, Agent, or Firm* — Wenderoth, Lind & Ponack, L.L.P.

(57) ABSTRACT

Displaying a status of a medical line includes receiving data characterizing a time at which use of the medical line commenced and a target usable time of the medical line. The medical line corresponds to a fluid transport channel for a patient. Using (i) the received data and (ii) a measure of elapsed time since use of the medical line commenced, the status of the medical line is determined that characterizes (a) a time until the target usable time of the medical line will be reached or (b) whether the target usable time of the medical line has been reached. A graphical user interface (GUI) element representing the status of the medical line as a function of time is displayed in a graphical user interface (GUI) display space. Related apparatus, systems, techniques and articles are also described.

17 Claims, 19 Drawing Sheets

(56) References Cited

U.S. PATENT DOCUMENTS

| | | |
|---|---|---|
| 2007/0282251 A1 | 12/2007 | Barvais et al. |
| 2009/0214625 A1* | 8/2009 | Nakayama ........... A61K 9/0009 424/449 |
| 2010/0073171 A1* | 3/2010 | Frinak ................. A61M 1/3653 340/573.1 |
| 2012/0138533 A1* | 6/2012 | Curtis .................... A61M 1/16 210/646 |

* cited by examiner

DISPLAYING STATUS OF MEDICAL LINES

TECHNICAL FIELD

The subject matter described herein relates to providing a graphical indication for displaying the status of schedulable items, such as medical fluid transport channels (e.g., medical lines) that are replaced according to a schedule.

BACKGROUND

A catheter is a tube that can be inserted in the body to treat diseases or perform a surgical procedure. Catheters can be inserted into a body cavity, duct, or vessel. Catheters allow drainage, administration of fluids or gases, access by surgical instruments, and can perform a wide variety of other tasks. By modifying the material or adjusting catheter-manufacturing processes, it is possible to tailor catheters for cardiovascular, urological, gastrointestinal, neurovascular, ophthalmic, and the like applications.

In many instances, a catheter is a thin, flexible tube although catheters are available in varying levels of stiffness depending on the application. An indwelling catheter is a catheter left inside the body, either temporarily or permanently. A catheter is a type of medical line, which can include fluid transport channels such as feeding tubes, drains, intravenous lines, and the like. However, patients having medical lines can be susceptible to infection.

SUMMARY

In an aspect, displaying a status of a medical line includes receiving data characterizing a time at which use of the medical line commenced and a target usable time of the medical line. The medical line corresponds to a fluid transport channel for a patient. Using (i) the received data and (ii) a measure of elapsed time since use of the medical line commenced, the status of the medical line is determined that characterizes (a) a time until the target usable time of the medical line will be reached or (b) whether the target usable time of the medical line has been reached. A graphical user interface (GUI) element representing the status of the medical line as a function of time is displayed in a graphical user interface (GUI) display space.

One or more of the following features can be included in any feasible combination. For example, the GUI element can be displayed as one or more color coded blocks horizontally arranged with respect to one another. Each color coded block can represent the status at discrete times. A graph with time indicia can be displayed with the GUI element. The status of the medical line can be dynamically determined. The GUI element can be updated with the status of the medical line over time.

The GUI element can be displayed as one or more color coded blocks and one or more of the blocks represent historical status of the medical line as a function of time. The GUI element can be displayed as one or more color coded blocks and one or more of the blocks represent a future status of the medical line as a function of time, the future status indicating expiration of the target usable time of the medical line. A characteristic of the GUI element can indicate that the target usable time of the medical line is presently not reached, is approaching, or is past. The GUI display space can be contained on a display of a patient parameter monitor.

Data can be received characterizing the medical line has been removed. The GUI element can be updated to include a block representing removal of the medical line as a function of time. Data can be received characterizing a second time at which use of a replacement medical line commenced and a target usable time of the replacement medical line. The replacement medical line can correspond to a second fluid transport channel for the patient. The GUI element can be updated to display the replacement medical line status.

The medical line can be selected from one or more of a catheter line, a feeding tube, a drain, and an intravenous line. An alarm can be generated when the target usable time of the medical line is reached. The steps of receiving, determining, and displaying can be concurrently performed for each of a plurality of medical lines corresponding to respective fluid transport channels for the patient.

Non-transitory computer program products (i.e., physically embodied computer program products) are also described that store instructions, which when executed by one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The subject matter described herein provides many technical advantages. For example, health care providers (such as nurses, doctors, and the like) can determine the status of a patient's medical lines easily and quickly (e.g., at a glance). The status of a patient's medical lines can be determined automatically and can be dynamically updated to ensure that the displayed status is current.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

Like reference symbols in the various drawings indicate like elements.

DETAILED DESCRIPTION

Figure 1:
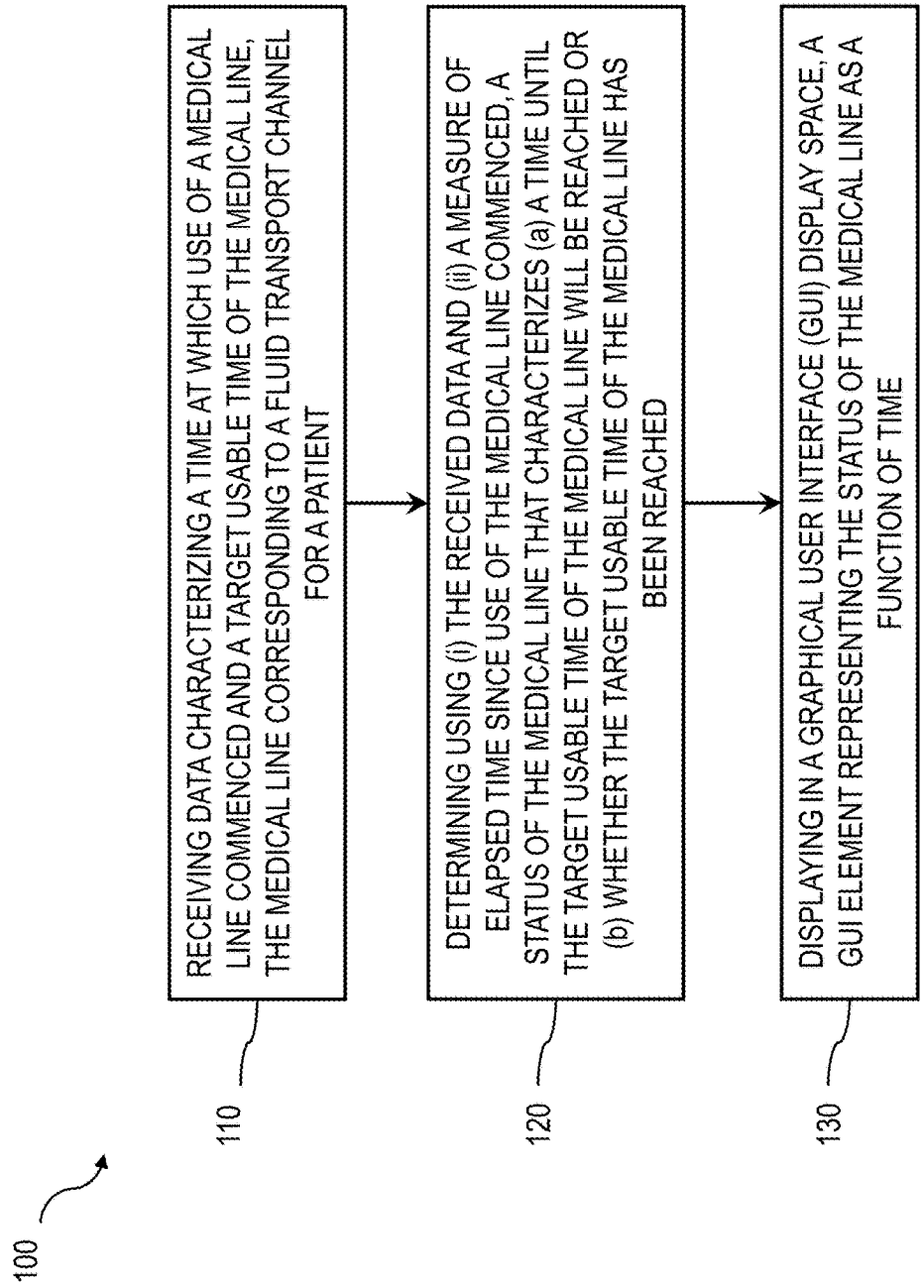
FIG. 1 is a process flow diagram illustrating a method of displaying graphical representations of medical line status as a function of time.

FIG. 1 is a process flow diagram illustrating a method 100 of displaying graphical representations of medical line status as a function of time. Healthcare providers routinely replace or remove medical lines according to a schedule and failure to comply with the schedule can lead to infection, which complicates patient treatment. Monitoring of medical line status can be challenging, for example, because it may require fastidious record keeping by healthcare personnel. The current subject matter can enable automatic and dynamic determination and display of current, future, and/or historical medical line status, including whether or not a healthcare worker should replace the medical line and/or how soon the healthcare worker should replace the medical line.

At 110, data is received characterizing a time at which use of a medical line commenced and a target usable time of the medical line. Medical lines can include fluid transport channels such as catheter lines, feeding tubes, drains, intravenous lines, and the like. Medical lines typically have an associated target usable time or standardized protocol, which can define a period of time the medical lines can be used on a patient before risking infection (e.g., useful life). For example, some intravenous catheters should be replaced every 24 hours.

The data can be received from, for example, a computer system in which a user provides input when the medical line is inserted into the patient. The user can also provide a description of when the medical line was inserted after the line was inserted. The target usable time of the medical line may be received from a database and/or input by the user. The target usable time of the medical line as well as attributes such as a label and line type may be selected from a list of attributes previously specified by an administrator to reduce user error.

At 120, a status of the medical line that characterizes a time until the target usable time of the medical line will be reached or whether the target usable time of the medical line has been reach can be determined. For example, the status can indicate that the target usable time is presently not reached (e.g., the medical line does not have to be replaced), the target usable time is approaching (e.g., the medical line has been used on the patient for more than a predefined portion of the target usable time, for example, greater than 80% of the target usable time), and/or that the target usable time has passed (e.g., the medical line should be replaced immediately). Other medical line statuses are possible.

The determination can be performed using the received data and a measure of elapsed time since use of the medical line commenced. For example, a difference between the present time and time use of the medical line commenced can be compared with the target usable time of the medical line.

At 130, a graphical user (GUI) element representing the status of the medical line as a function of time can be displayed. The GUI element can display in a GUI display space. The GUI element can include one or more color coded blocks that can represent one or more of historical status of the medical line as a function of time, the present status of the medical line as a function of time, and a future status of the medical line as a function of time. The future status can indicate an expiration of the target usable time of the medical line. The position, sequence, and coloring of the color-coded boxes or bars can depict the status of one or more medical lines. In some implementations, the steps of receiving, determining, and displaying is concurrently performed for each of a plurality of medical lines corresponding to respective fluid transport channels for the patient.

In some implementations, the GUI elements can display as a function of time in an intuitive and easy to understand manner and thus the current subject matter can allow physicians and other health care providers to determine the status of the associated medical line and take or plan for any appropriate action. By providing a better understanding of medical line status, health care providers can remove and/or replace medical lines according to their protocols to reduce infections (and/or other undesirable situations).

Figure 2:
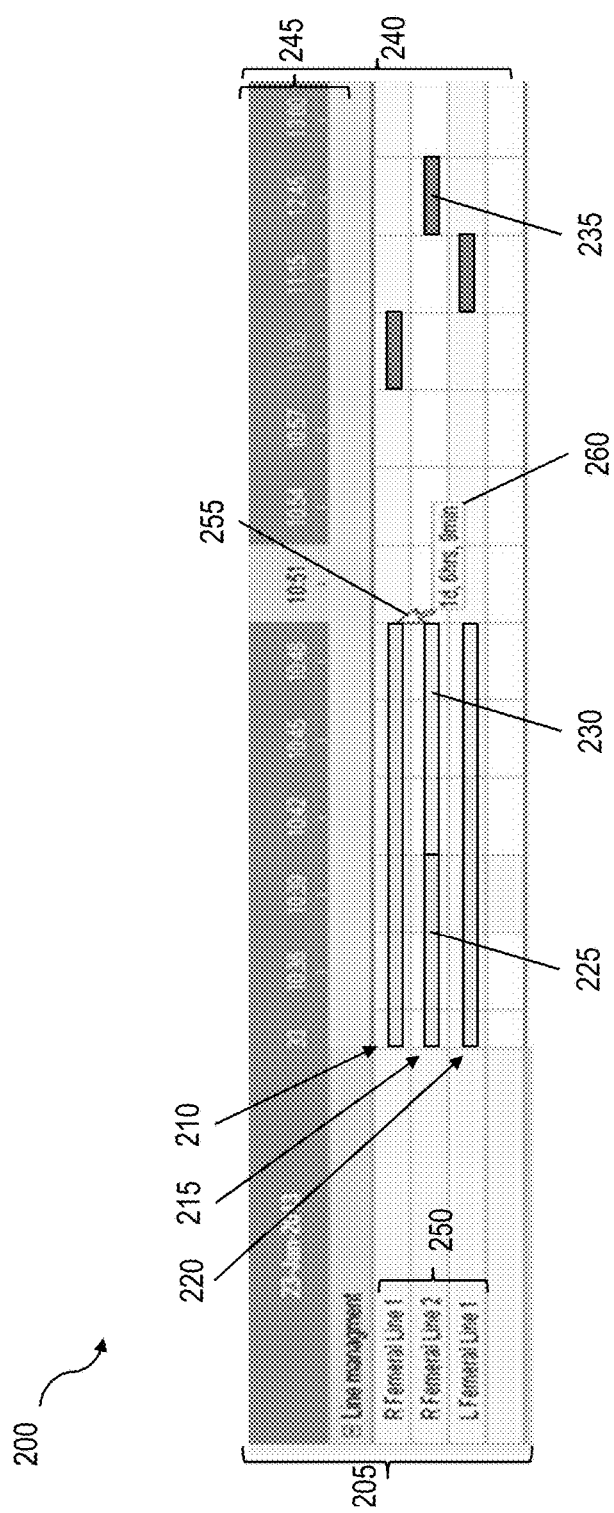
FIG. 2 is an image in an example GUI display space illustrating three GUI elements representing the status of three medical lines as a function of time.

For example, FIG. 2 is an image 200 in an example GUI display space 205 illustrating three GUI elements (210, 215, and 220) representing the status of three medical lines as a function of time. Each GUI element (210, 215, and 220) has one or more color-coded blocks or bars horizontally arranged with respect to one another. Each color-coded block or bar can represent the status at discrete times. For example, GUI element 215 includes a first block 225 displayed with a green color and represents historical status of the associated medical line. The color green can indicate that the target usable time of the medical line has not elapsed and will not be elapsing soon (e.g., less than a predetermined percentage of the target usable time has elapsed). GUI element 215 also includes a second block 230 displayed with a yellow color representing both historical and current status of the associated medical line. The color yellow can indicate that the target usable time of the medical line has not elapsed but may elapse soon (for example, a predetermined percentage of the target usable time has elapsed). GUI element 215 also includes a third block 235 displayed with a red color representing a future status of the associated medical line. The color red can represent the elapse or expiration of the target usable time of the associated medical line. In some implementations, the future status does not display and different color-coding may be used.

Each color-coded block can represent the status at discrete times. The GUI elements (210, 215, and 220) display on a graph 240 (also referred to herein as a flow sheet) with cells and time indicia 245 indicating present, past, and future time points. The time indicia show discrete points in time for a column of cells and thus the color coded blocks can represent status for discrete periods of time (e.g., in FIG. 2, each time indicia 245 and associated cell corresponds to 3 minutes of time, and each cell can be filled in on a column basis with no partial columns). Graph 240 can include line labels 250 characterizing the associated medical line. A user can input and/or specify the characterization (e.g., line title). A user can manipulate a cursor 255, which when the cursor 255 hovers over a color-coded block, a tool-tip 260 can display showing information about the associated medical line. For example, in FIG. 2, the tool-tip 260 illustrates the amount of time the medical line has been in use. If a new or replacement medical line starts, the tool-tip 260 can display the information for the GUI element over which the cursor 255 is hovering, even if a healthcare provider has removed the associated medical line.

In operation, the status of each medical line can be dynamically determined over time. GUI elements (210, 215, and 220) can be updated with the status of the medical line accordingly and over time. For example, a medical line first inserted can be displayed as a green block. As time goes on, the GUI elements can be updated so that the cells corresponding to the present or most recent discrete time period can be filled in with the appropriate color. The GUI element can display as one or more blocks or bars colored green, then yellow, then red, depending on the status. When to display green, yellow, or red can vary. In some implementations, the GUI element displays (at the current or most recent time) as green until 80% of the target usable time of the associated medical line has elapsed. Then yellow is displayed (at the current or most recent time) until 100% of the target usable time of the associated medical line has elapsed, after which red is displayed. Red can be displayed until data is received indicating that the associated medical line has been removed. Other colors and indicators are possible.

As another example that the status of each medical line can be dynamically determined over time, FIG. 2 illustrates the status of the medical lines up to time point "10:48." Three minutes later, the status of the medical line can be determined and GUI element 215 can be updated so that second block 230 extends to the adjacent region denoted by "10:51." In this example, the second block 230 remains yellow. In some implementations, another block may be displayed with a different color and representing a different status.

In some implementations, the cursor 255 can also be used for selecting and entering data (for example, that the associated medical line has been inserted/removed).

Figure 3:
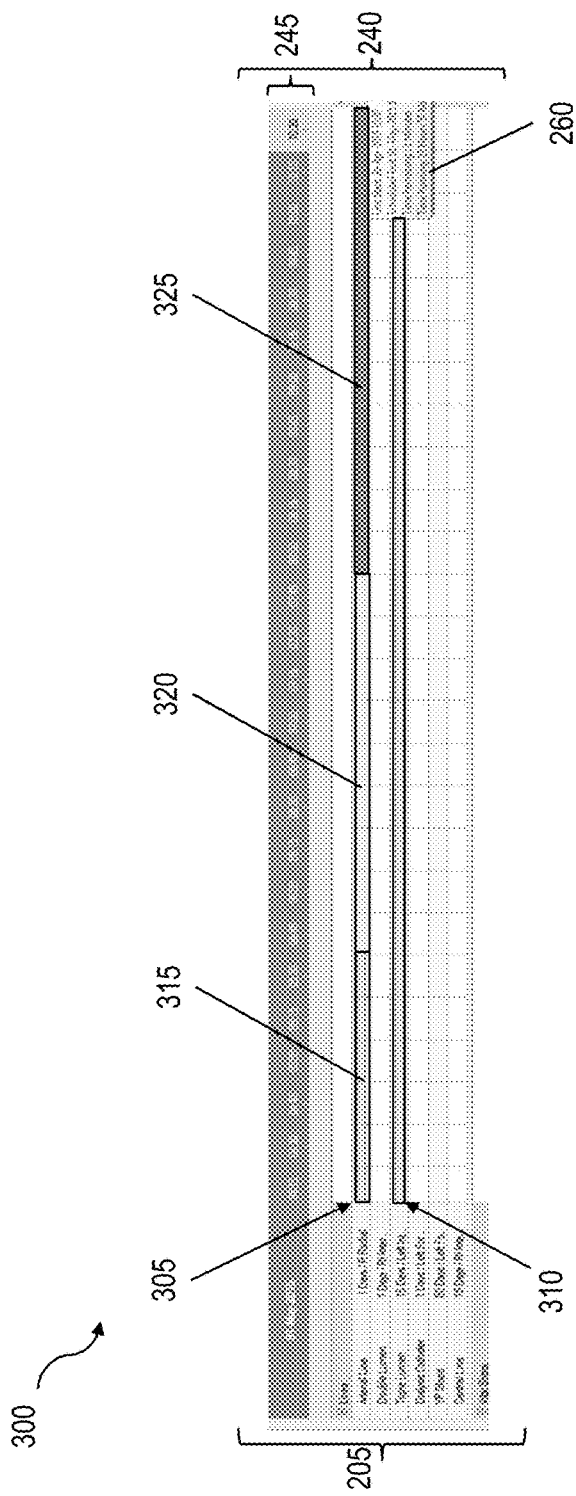
FIG. 3 is another image in the example GUI display space having two GUI elements representing the status of two medical lines as a function of time.

FIG. 3 is another image 300 in example GUI display space 205 illustrating having two GUI elements (first GUI element 305 and second GUI element 310) representing the status of two medical lines a function of time. In this example, the first GUI element 305 has a first block 315 (green), a second block 320 (yellow), and a third block 325 (red). Because the first GUI element 305 shows the target usable time has elapsed (two and a half hours previously) the associated medical line is in need of replacement.

Figure 4:
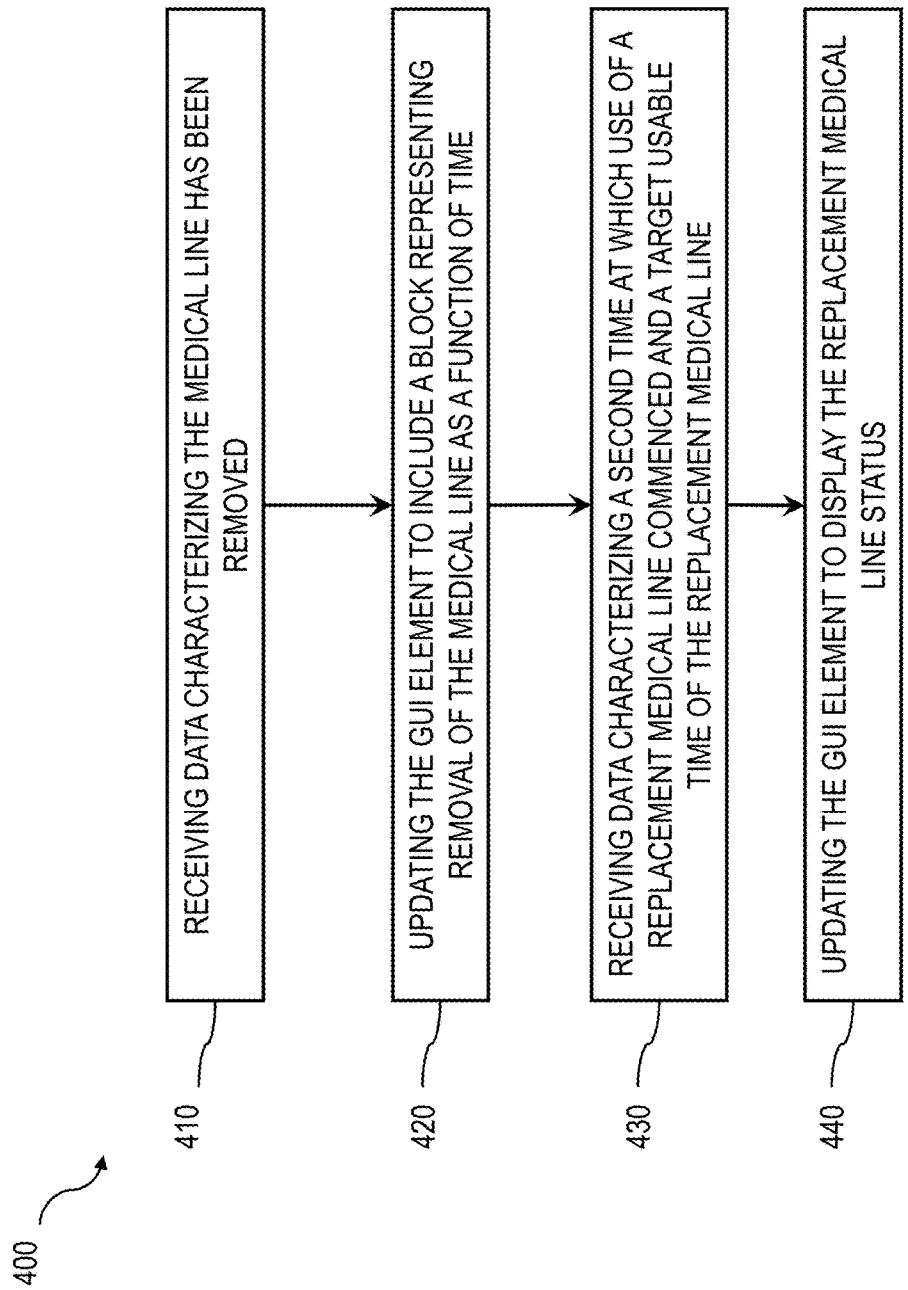
FIG. 4 is a process flow diagram illustrating a method of updating GUI elements.

FIG. 4 is a process flow diagram 400 illustrating a method of updating GUI elements. At 410, data can be received characterizing that the medical line has been removed. At 420, the associated GUI element can be updated to include a block representing removal of the medical line as a function of time. In some implementations, at 430, data can be received characterizing a second time at which use of a replacement medical line commenced and a target usable time of the replacement medical line. At 440, the GUI element can be updated to display the replacement medical line status.

Figure 5:
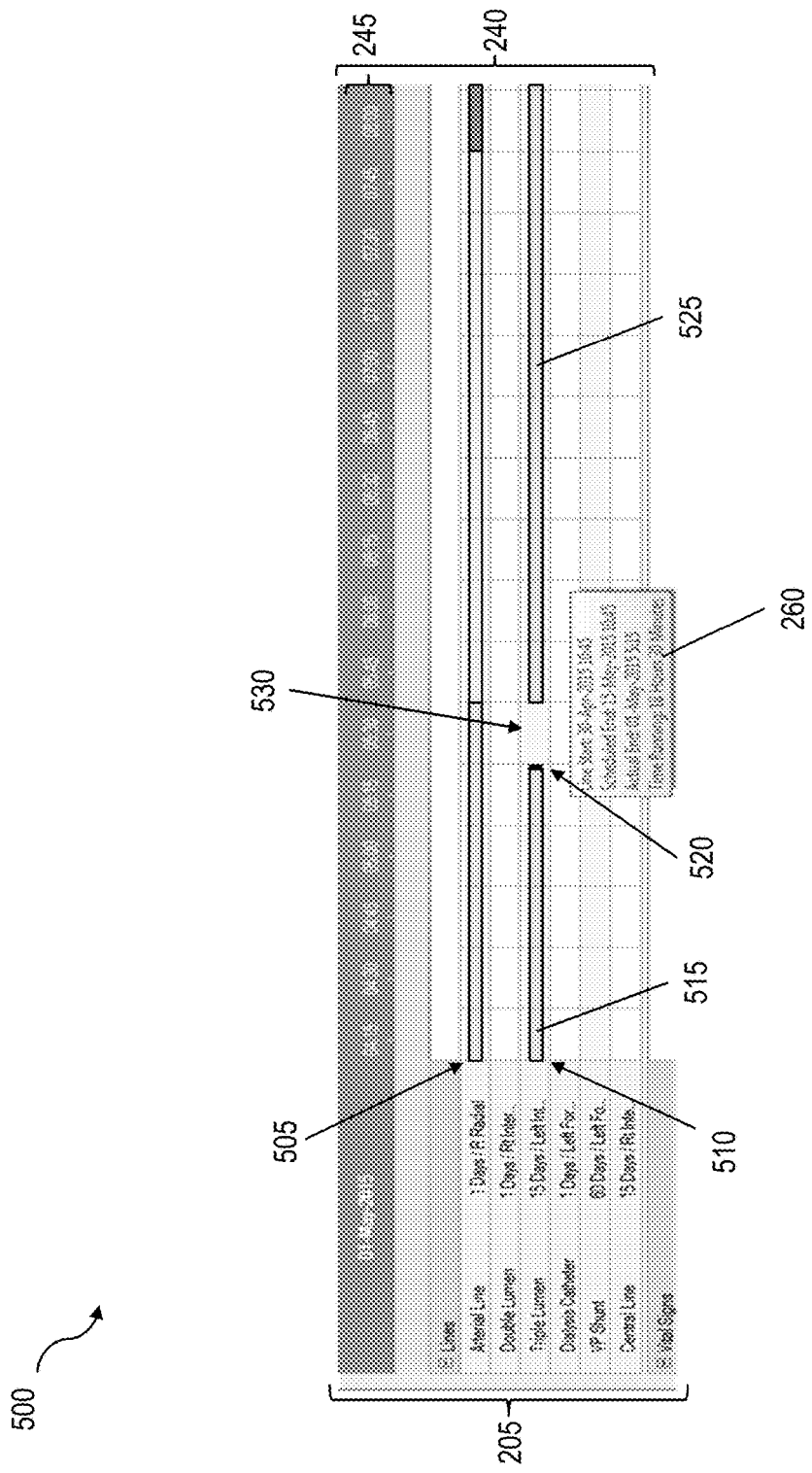
FIG. 5 is another image of the example GUI display space having two GUI elements representing the status of two medical lines as a function of time.

For example, FIG. 5 is another image 500 in example GUI display space 205 having two GUI elements (first GUI element 505 and second GUI element 510) representing the status of two medical lines as a function of time. In this example, a medical line has been replaced. The second GUI element 510 includes a first block 515, a removal block 520 and a replacement line block 525. The first block 515 is associated with a first medical line. Removal block 520 indicates that a healthcare provider removed the medical line from the patient. Removal block 520 is illustrated as a thin black box or line. A gap 530 between removal block 520 and replacement line block 525 represents a period of time in which no line was in use. The replacement line block 525 represents the newly inserted medical line. A user can input data characterizing that a healthcare provider removed the first medical line and/or when they removed the first medical line. A user can also input data characterizing that a healthcare provider inserted a second medical line and/or when they inserted the second medical line. If data is received indicating that a medical line is removed before the target usable time has elapsed, the red block indicating future status can be removed (e.g., no longer displayed).

Figure 19:
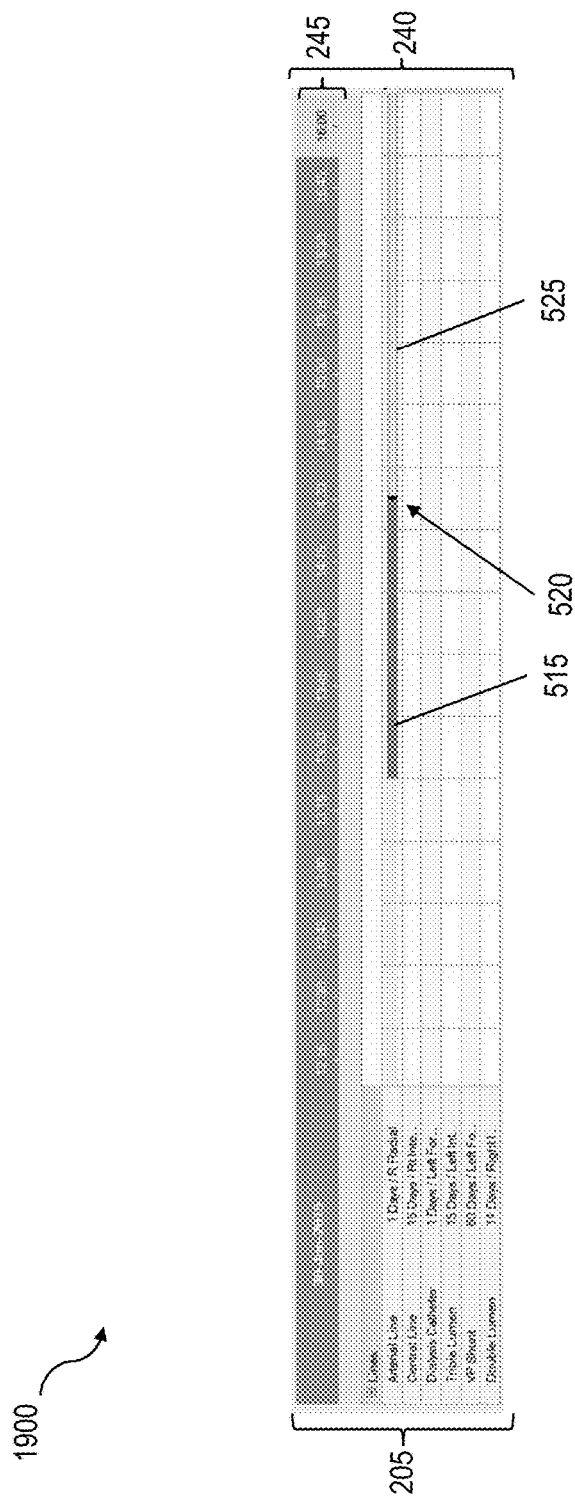
FIG. 19 is an image of the example GUI display space illustrating replacement of a line where no gap is displayed.

In some implementations, a gap 530 between removal block 520 and replacement line block 525 does not need to be illustrated to represent a period of time in which no line was in use. This may occur, for example, when the period in which no line was in use is less than the length of the discrete time periods (as represented by cells of graph 240). FIG. 19 is an example image 1900 illustrating replacement of a line where no gap 530 is displayed. In the example, the discrete time periods are each 15 minutes and so no gap 530 is displayed if the replacement medical line was inserted less than 15 minutes after the previous medical line was removed. In other words, the length of the discrete time periods may be too coarse to represent any gap 530 in medical line use.

Figure 6:
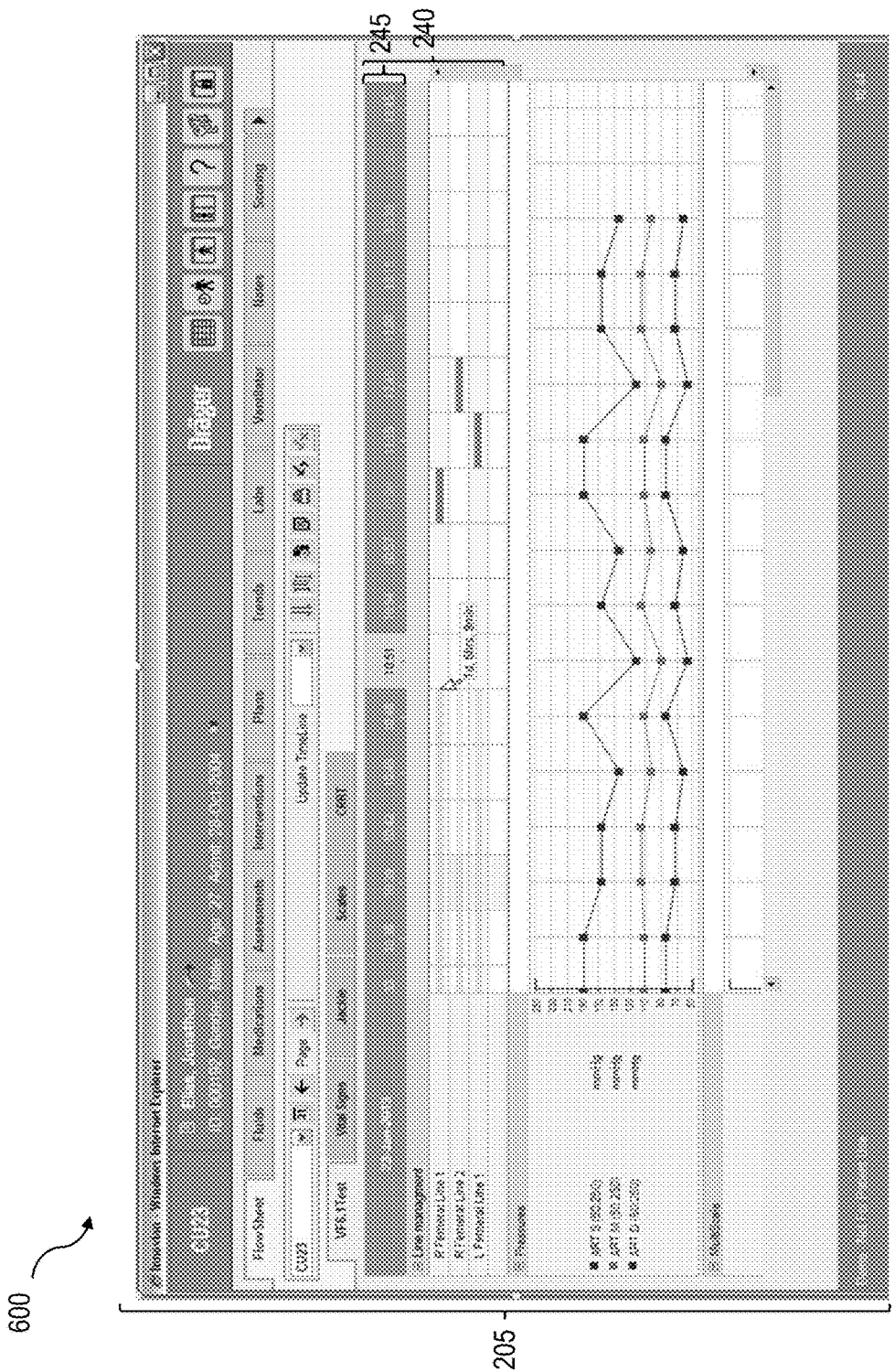
FIG. 6 is another image of the example GUI display space illustrating, in addition to GUI elements, that additional information may be displayed alongside the graph with GUI elements.
Figure 7:
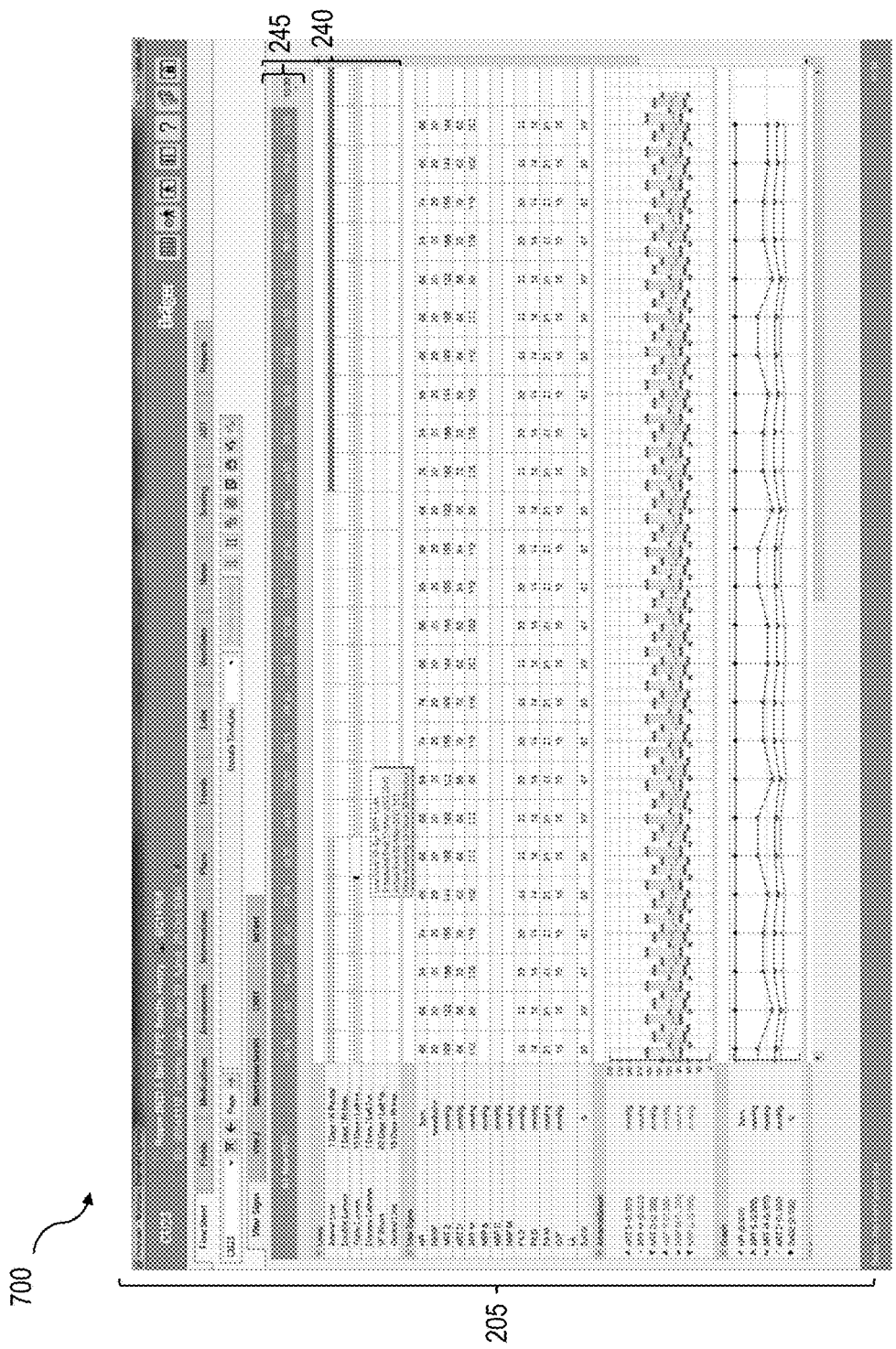
FIG. 7 is another image of the example GUI display space illustrating, in addition to GUI elements representing medical line status, that additional information may be displayed alongside the graph with GUI elements.

FIG. 6 is another image 600 in example GUI display space 205 illustrating, in addition to GUI elements, that additional information may be displayed alongside the graph 240 with GUI elements. In the example of FIG. 6, arterial pressures are displayed as a function of time. This patient parameter data may be received automatically, for example, using a patient parameter monitor having one or more sensors. FIG. 7 is another image 700 in example GUI display space 205 illustrating, in addition to GUI elements representing medical line status, that additional information may be displayed alongside the graph 240 with GUI elements. In the example of FIG. 7, vital signs (such as heart rate and other patient physiological parameters) are displayed using different visualization techniques.

Figure 8:
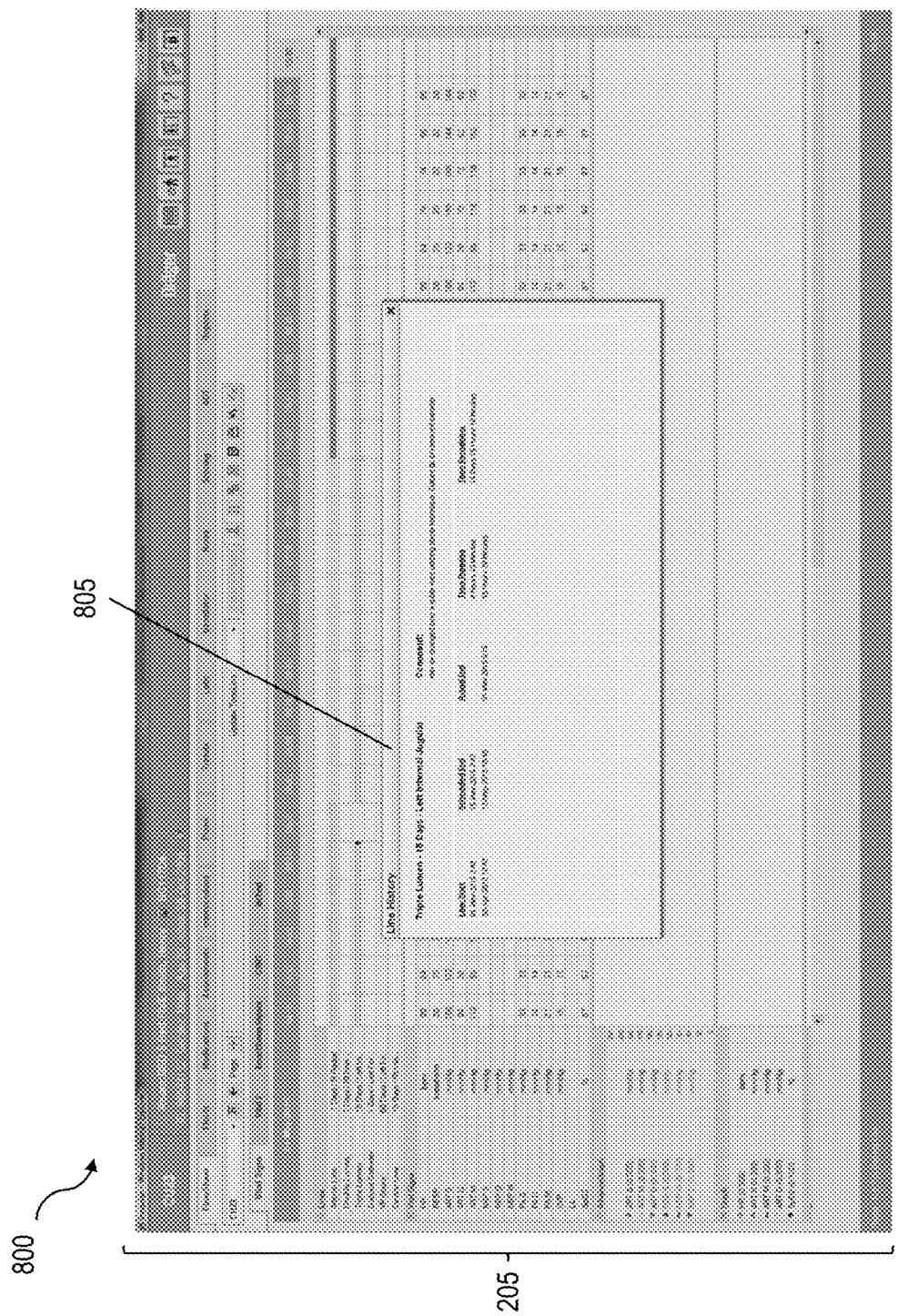
FIG. 8 is another image of the example GUI display space illustrating that a status history summary panel may be displayed.

FIG. 8 is another image 800 in example GUI display space 205 illustrating that a status history summary panel 805 may be displayed. The status history summary panel 805 shows when each line was started, when each line is scheduled to end, when each line actually ended (e.g., was removed), the time elapsed that the medical lines have been or were in use, and the time remaining until the target usable time of any medical lines in use will be reached. The status history summary panel 805 can also include comments related to one or more of the medical lines.

Figure 9:
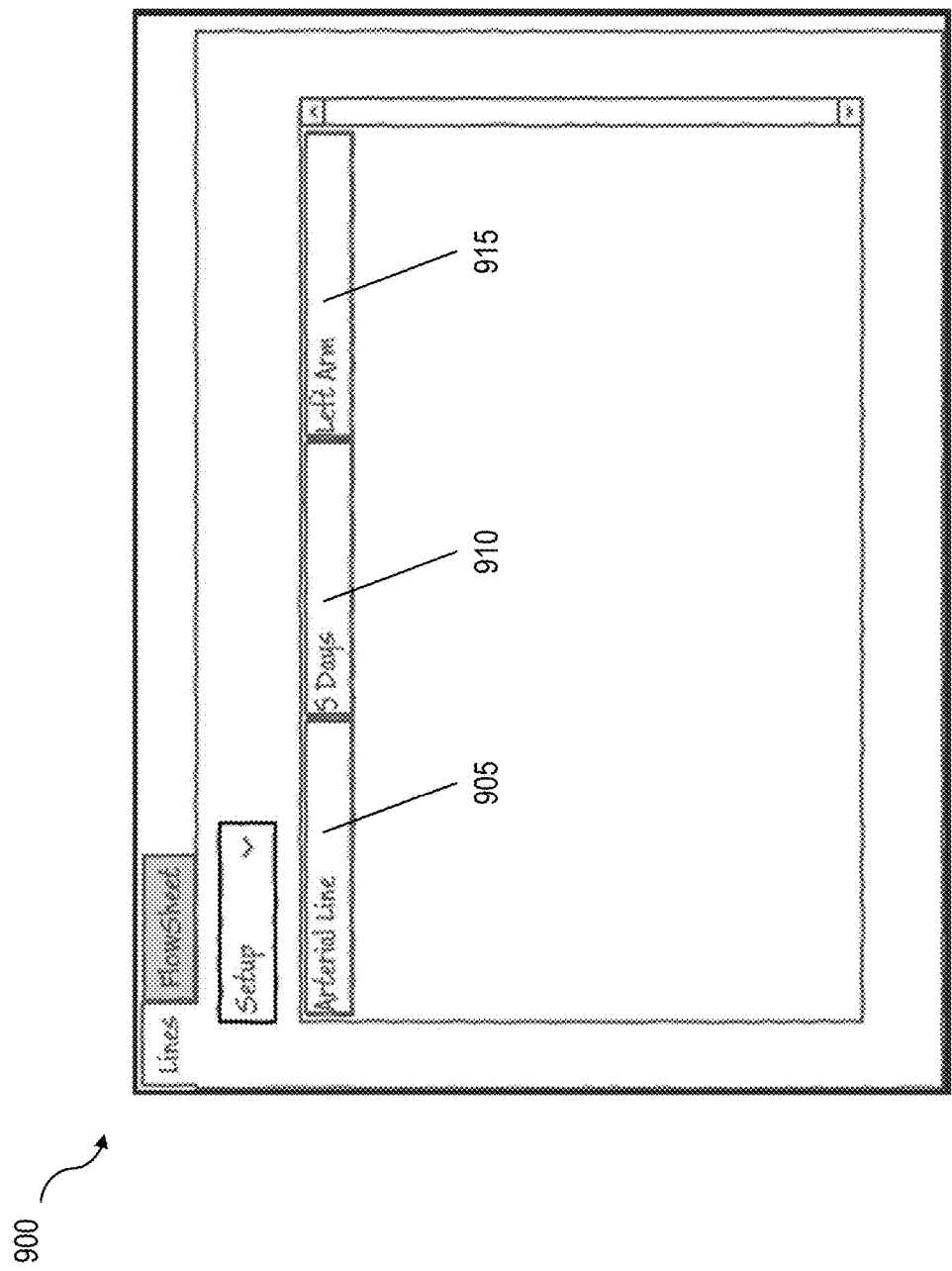
FIG. 9 is a setup GUI for performing a system-wide setup of some aspects of the current subject matter.
Figure 10:
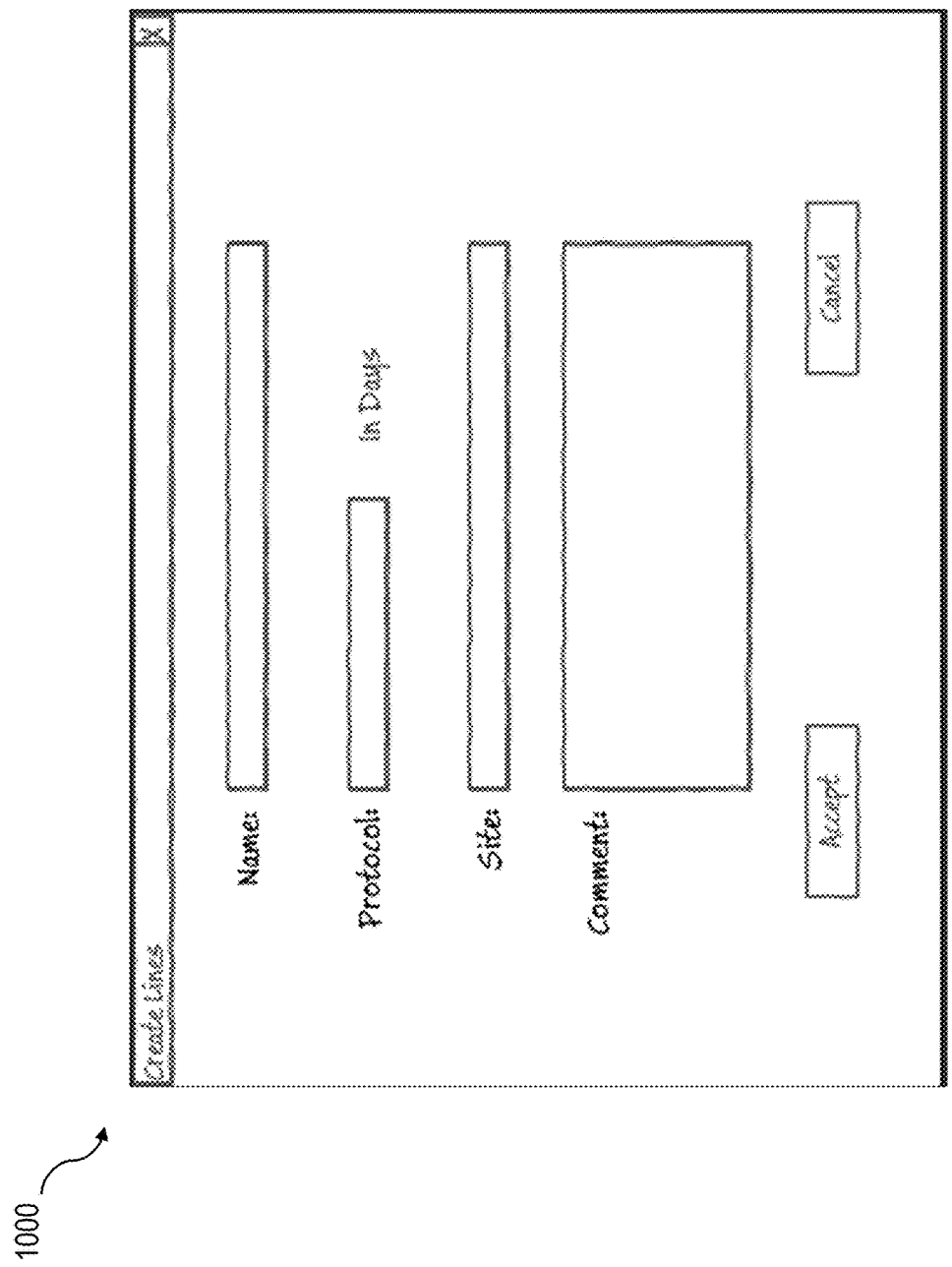
FIGS. 10 and 11 are setup GUIs for specifying attributes of the medical lines.
Figure 11:
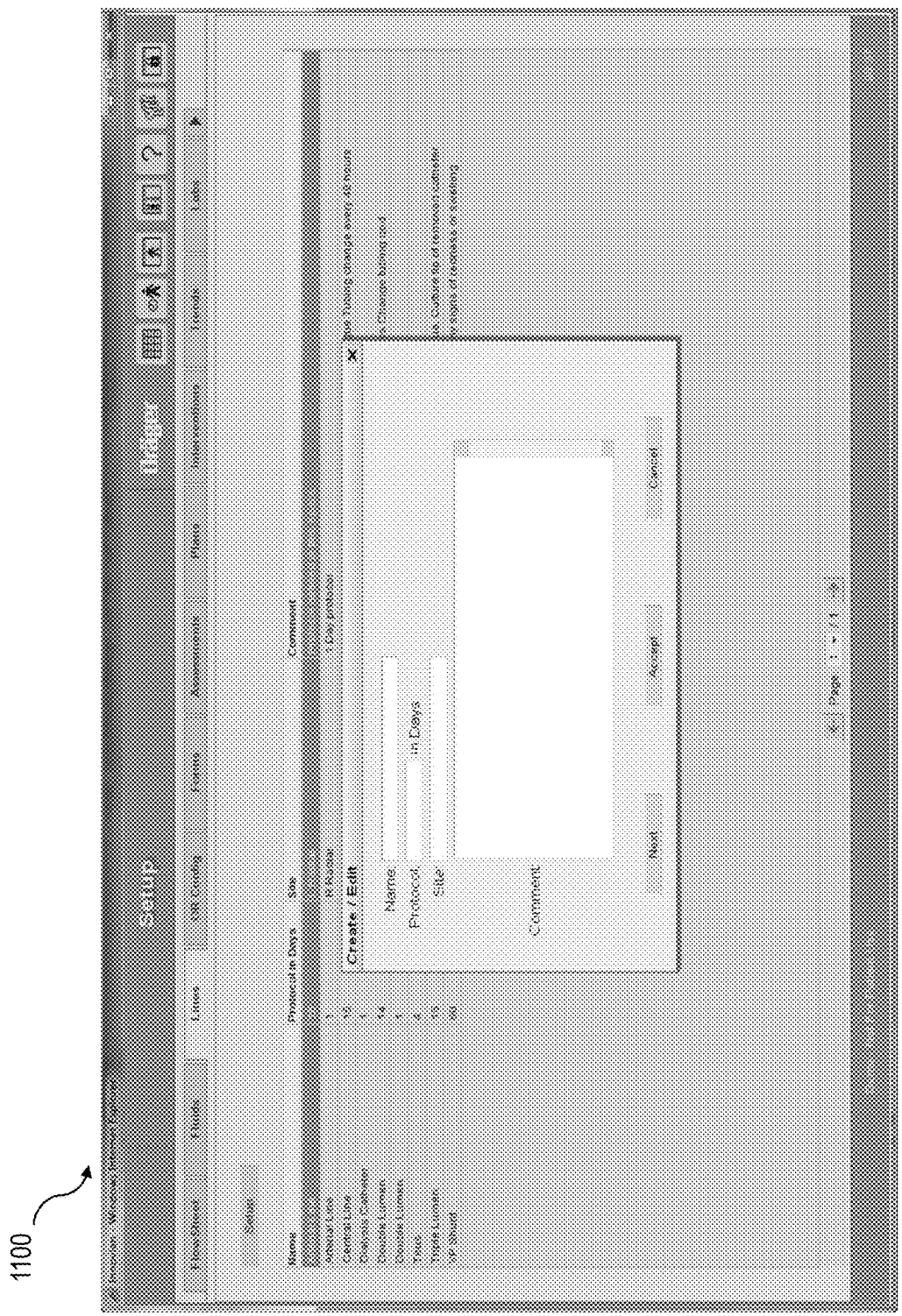

FIG. 9 is a setup GUI 900 for performing a system-wide setup of some aspects of the current subject matter. The setup GUI 900 can provide for system administrators to specify line attributes that health care providers can later select. The setup GUI 900 can allow for an administrator or another user to configure the current subject matter so only certain types of medical lines with predefined attributes can be selected for use (for example, corresponding to the medical lines available for use at a particular healthcare facility). The setup GUI 900 can include a list of configured medical lines that specifies line name 905, a target usable time 910, and a location of the medical line 915. FIGS. 10 and 11 are setup GUIs 1000 and 1100, respectively, for specifying attributes of the medical lines. A user can specify the name, protocol, location of line, and any comments.

Figure 12:
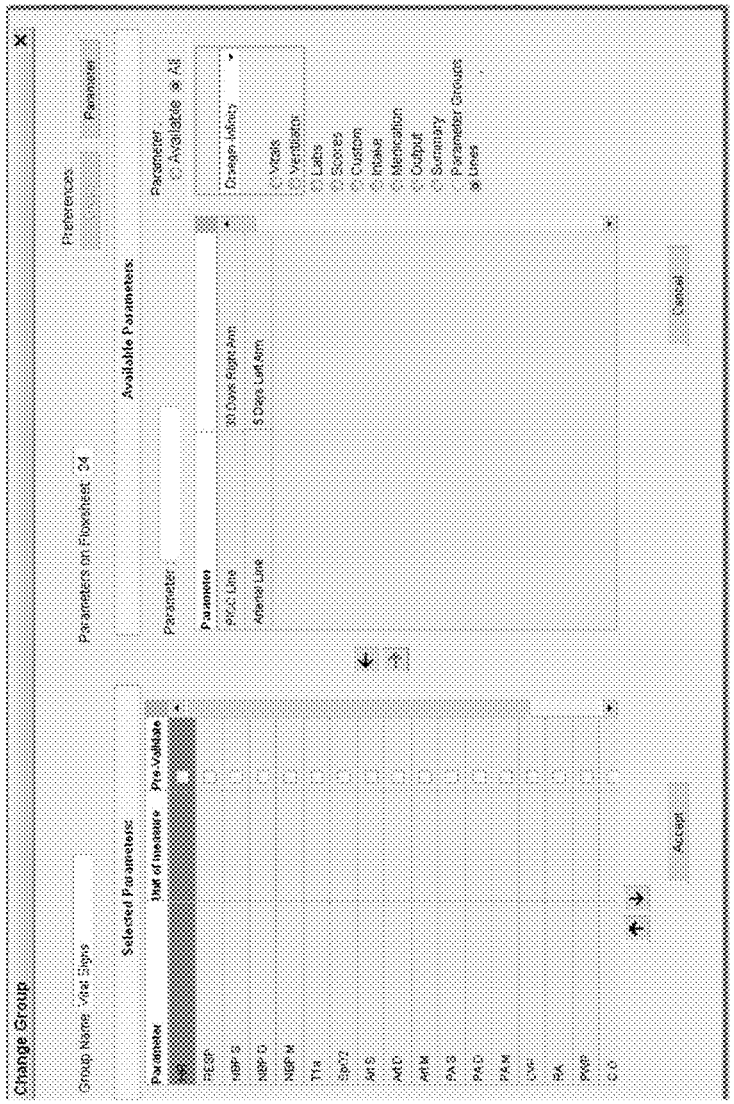
FIG. 12 is a setup GUI for specifying which medical line status' are to be displayed in the GUI display.
Figure 13:
FIG. 13 is another example implementation of the setup GUI of FIG. 12.

FIG. 12 is a setup GUI 1200 for specifying which medical line status' are to be displayed in the GUI display space 205. The setup GUI 1200 can configure the GUI display space 205, and allows for selection and ordering of various medical lines and physiological parameters. FIG. 13 is another example implementation of the setup GUI 1200 of FIG. 12.

Figure 14:
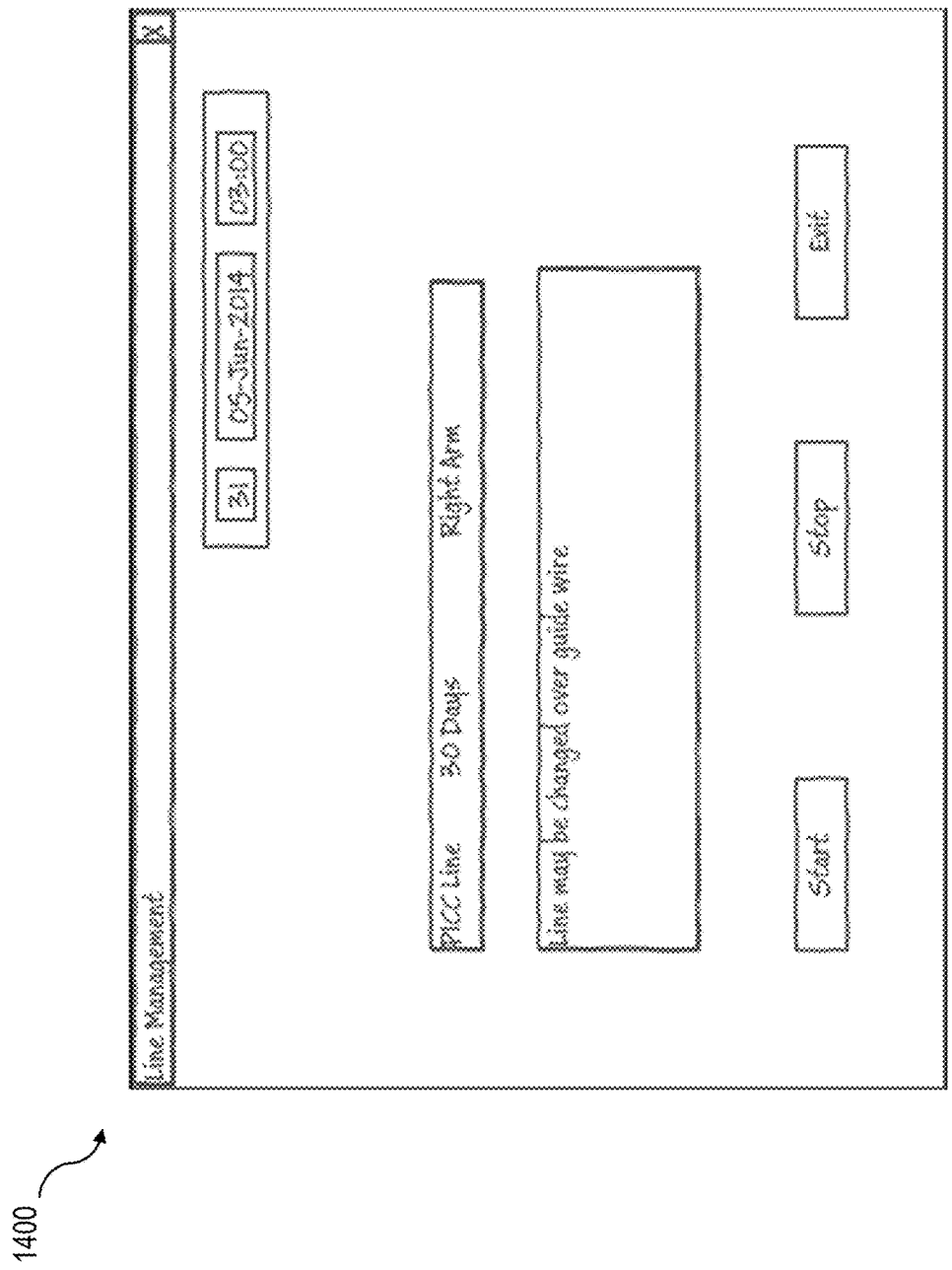
FIG. 14 is a line management GUI for specifying the start of a medical line

FIG. 14 is a line management GUI 1400 for specifying the start of a medical line. The line management GUI 1400 may be presented to a user, for example, by double clicking the cursor 255 on a cell in the graph 240 corresponding to the associated medical line. The line management GUI 1400 can include an interface for selecting the medical line (from a list of previously specified available medical lines), providing comments, and specifying time of line start and stop.

Figure 15:
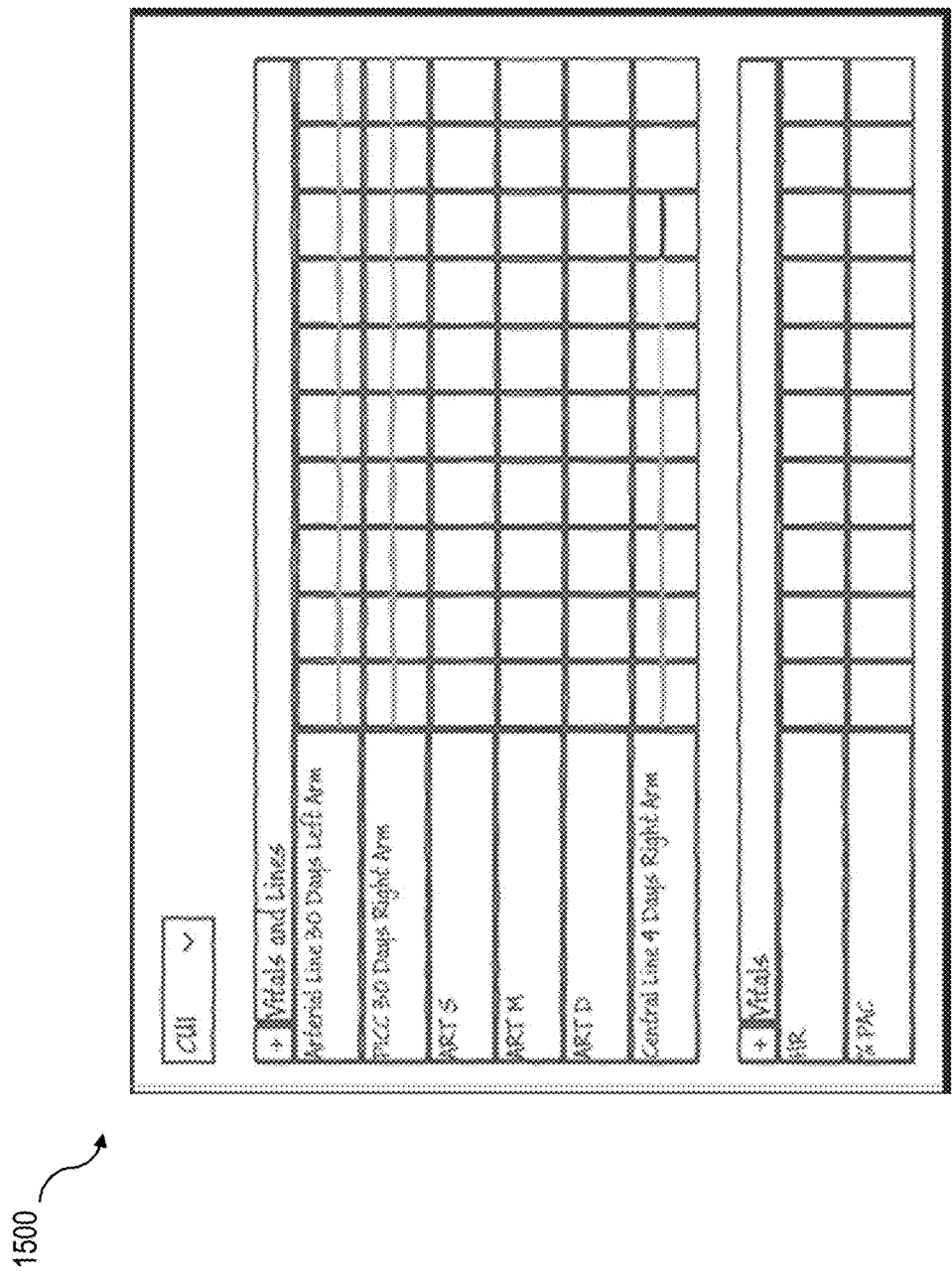
FIG. 15 illustrates a GUI at a pre-transfer stage of a patient transfer between care units in a healthcare facility.
Figure 16:
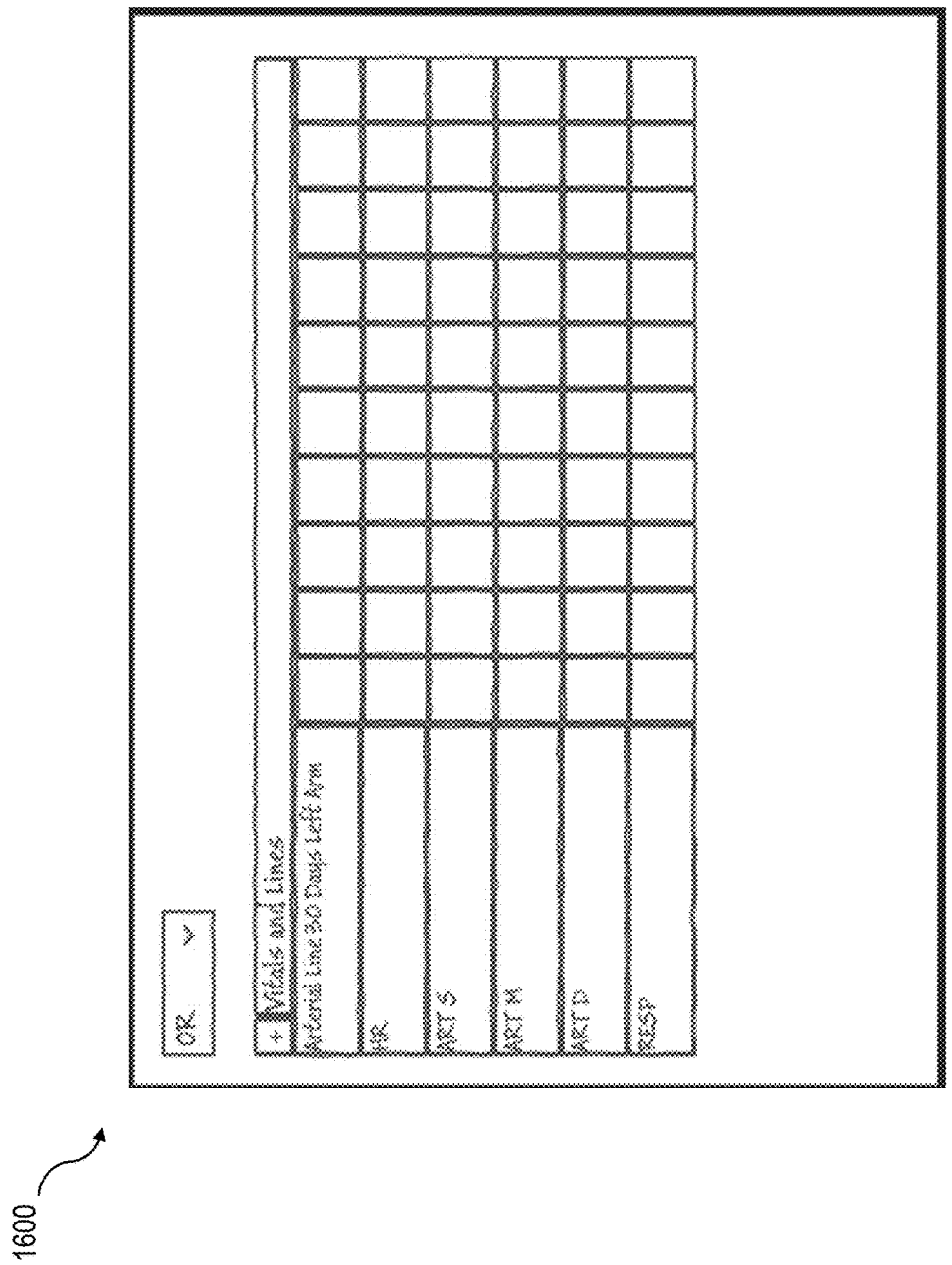
FIG. 16 illustrates a pre-configured GUI template for the "OR" care unit.
Figure 17:
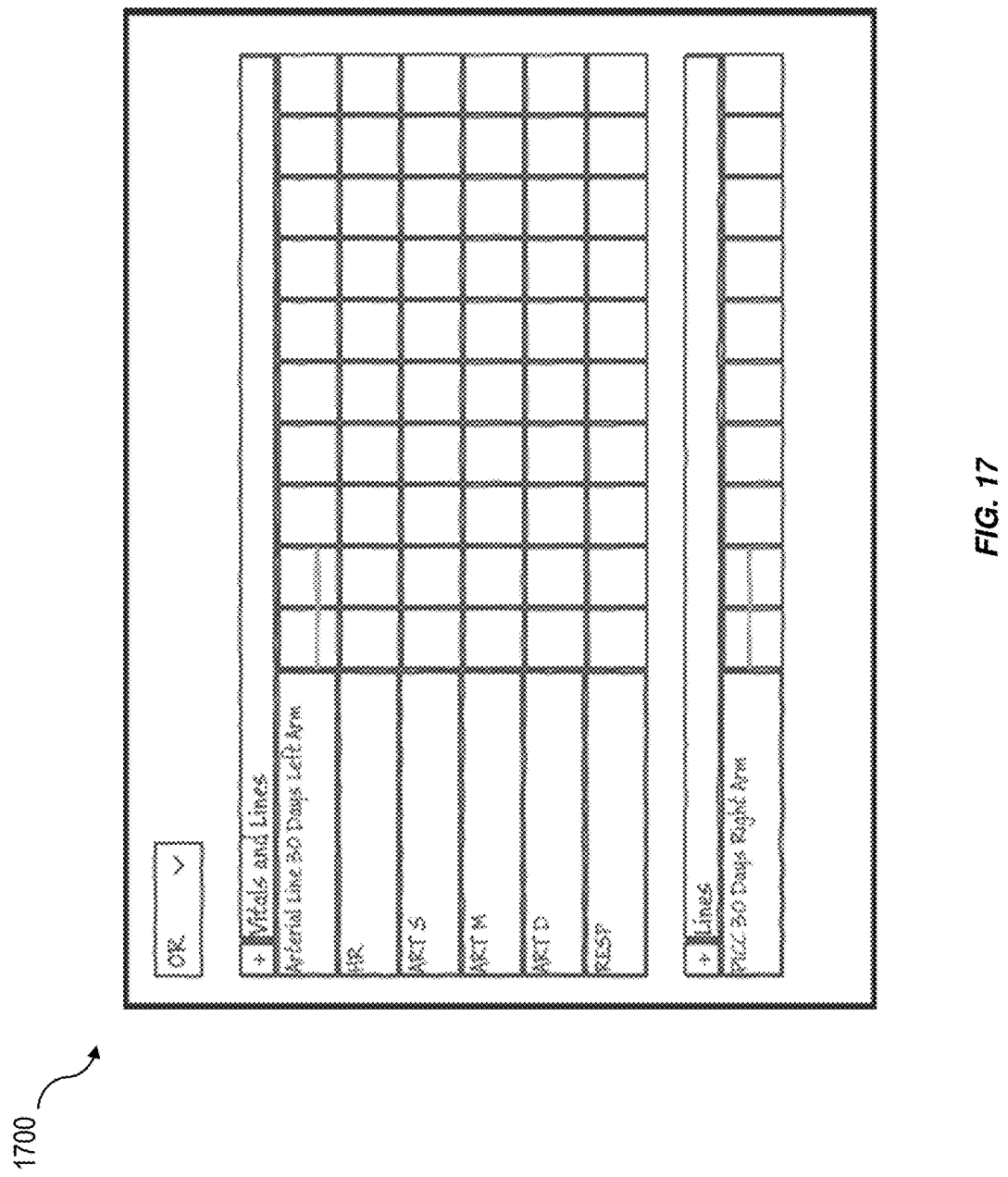
FIG. 17 illustrates a GUI at a post-transfer state of a patient transfer between care units in a healthcare facility.

In some implementations, a patient may transfer between care units within a healthcare facility while having inserted medical lines. In order to handle the transfer, the medical line status may need to transfer between GUI display spaces located on different displays (for example, on different patient monitor displays). FIGS. 15-17 illustrate GUIs 1500, 1600 and 1700, at different stages of a patient transfer between care units in a facility. If a patient transfers with an active line, the line should continue in the new care unit. If the medical line is already in the GUI display space, the medical line will continue to be documented in the new care unit in the position in which it existed in the new care unit. If the line is not in the new care unit flow sheet, a new GUI display space called Lines can be added and the active line from the previous care unit can be continued in the new care unit. For example if a flow sheet in "CU1" has 3 lines but only 2 are active as shown in FIG. 15, and the patient is transferred to another care unit (e.g., "OR"), then the resulting flow sheet is displayed in FIG. 17. In the new OR care unit the Arterial Line was already configured, as shown in FIG. 16, which depicts a pre-configured GUI template for the "OR" care unit, but the peripherally inserted central catheter (PICC) Line is not. After the patient transfers, the Arterial Line continues in the pre-configured location but a new display space is created for the PICC Line, which was not originally configured in the care unit, as shown in FIG. 17.

Figure 18:
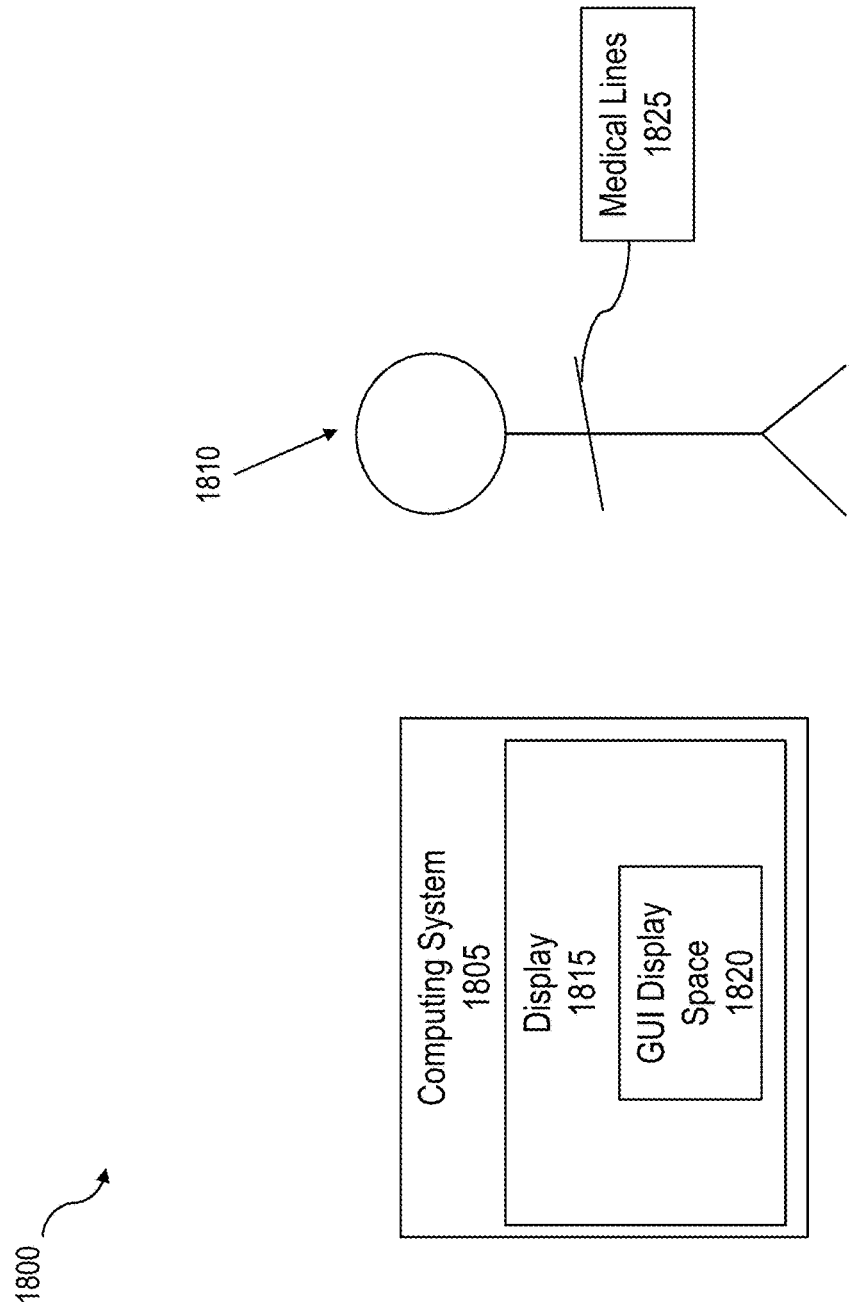
FIG. 18 is a system block diagram illustrating a system for providing a graphical indication for displaying the status of schedulable items, and more specifically, displaying the status of medical lines in a healthcare setting.

FIG. 18 is a system block diagram illustrating a system 1800 for providing a graphical indication for displaying the status of schedulable items, and more specifically, displaying the status of medical lines in a healthcare setting. The system 1800 includes a computing system 1805, which can include a patient parameter monitor having one or more sensors for monitoring physiological parameters of a patient 1810. The patient 1810 can be using (e.g., attached to) one or more medical lines 1825. The computing system 1805 can include a display 1815, which can render GUI elements indicating the status of medical lines in a GUI display space 1820. Thus, the GUI display space 1820 can be contained on the display 1815 of the computing system 1805 (e.g., a patient parameter monitor).

In some implementations, an alarm can be generated when the target usable time of the medical line is reached. The alarm may be, for example, visual, audio, mechanical (e.g., vibration), and the like. Alarms may be generated when other criterion or conditions are satisfied. An alarm can include a popup task reminder that presents at an appropriate time. Other implementations are possible.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method for displaying a status of a medical line, the method for implementation by at least one data processor forming part of one or more computing systems, the method comprising:
    receiving data characterizing a time at which use of the medical line commenced and a target usable time of the medical line, the medical line corresponding to a fluid transport channel for a patient;
    determining, using (i) the received data and (ii) a measure of elapsed time since use of the medical line commenced, the status of the medical line that characterizes (a) a time until the target usable time of the medical line will be reached or (b) whether the target usable time of the medical line has been reached;
    displaying, in a graphical user interface (GUI) display space, a GUI element representing the status of the medical line as a function of time;
    receiving data indicating that the medical line has been removed; and
    updating the GUI display space to include (i) the GUI element as a first block associated with the medical line, (ii) a second block indicating a specific time of removal of the medical line, and (iii) a third block associated with a replacement medical line, wherein
    in the updated GUI space, the second block indicating the specific time of removal of the medical line is arranged between the first block and the third block, and
    the method further comprising:
        receiving, data characterizing a second time at which use of the replacement medical line commenced and a target usable time of the replacement medical line, the replacement medical line corresponding to a second fluid transport channel for the patient; and
        updating the GUI display space to display the replacement medical line status as the third block associated with the replacement medical line.

2. The method of claim 1, wherein the GUI element is displayed as one or more color coded blocks horizontally arranged with respect to one another, each color coded block representing the status at discrete times, and a graph with time indicia is displayed with the GUI element.

3. The method of claim 2, further comprising:
    dynamically determining the status of the medical line; and
    updating the GUI element with the status of the medical line over time.

4. The method of claim 1, wherein the GUI element is displayed as one or more color coded blocks and one or more of the blocks represent historical status of the medical line as a function of time.

5. The method of claim 1, wherein the GUI element is displayed as one or more color coded blocks and one or more of the blocks represent a future status of the medical line as a function of time, the future status indicating expiration of the target usable time of the medical line.

6. The method of claim 1, wherein a characteristic of the GUI element indicates that the target usable time of the medical line is presently not reached, is approaching, or is past.

7. The method of claim 1, wherein the GUI display space is contained on a display of a patient parameter monitor.

8. The method of claim 1, wherein the medical line is selected from one or more of a catheter line, a feeding tube, a drain, and an intravenous line.

9. The method of claim 1, further comprising:
    generating an alarm when the target usable time of the medical line is reached.

10. The method of claim 1, wherein the steps of receiving, determining, and displaying are concurrently performed for each of a plurality of medical lines corresponding to respective fluid transport channels for the patient.

11. A system for displaying a status of a medical line, the system comprising:
    at least one data processor;
    a display including a graphical user interface (GUI) display space; and
    memory storing instructions which, when executed by the at least one data processor, causes the at least one data processor to perform operations comprising:
        receiving data characterizing a time at which use of the medical line commenced and a target usable time of the medical line, the medical line corresponding to a fluid transport channel for a patient;

determining, using (i) the received data and (ii) a measure of elapsed time since use of the medical line commenced, the status of the medical line that characterizes (a) a time until the target usable time of the medical line will be reached or (b) whether the target usable time of the medical line has been reached;

displaying, in the graphical user interface (GUI) display space, a GUI element representing the status of the medical line as a function of time;

receiving data indicating that the medical line has been removed; and updating the GUI display space to include (i) the GUI element as a first block associated with the medical line, (ii) a second block indicating a specific time of removal of the medical line, and (iii) a third block associated with a replacement medical line, wherein in the updated GUI space, the second block indicating the specific time of removal of the medical line is arranged between the first block and the third block, and the operations further comprising:

receiving, data characterizing a second time at which use of the replacement medical line commenced and a target usable time of the replacement medical line, the replacement medical line corresponding to a second fluid transport channel for the patient; and updating the GUI display space to display the replacement medical line status as the third block associated with the replacement medical line.

12. The system of claim 11, wherein the GUI element is displayed as one or more color coded blocks horizontally arranged with respect to one another, each color coded block representing the status at discrete times, and a graph with time indicia is displayed with the GUI element.

13. The system of claim 12, the operations further comprising:

dynamically determining the status of the medical line; and updating the GUI element with the status of the medical line over time.

14. The system of claim 11, wherein the GUI element is displayed as one or more color coded blocks and one or more of the blocks represent historical status of the medical line as a function of time.

15. The system of claim 11, wherein the system is a patient parameter monitor.

16. The system of claim 11, wherein the medical line is selected from one or more of a catheter line, a feeding tube, a drain, and an intravenous line.

17. The system of claim 11, wherein the steps of receiving, determining, and displaying are concurrently performed for each of a plurality of medical lines corresponding to respective fluid transport channels for the patient.

* * * * *